US009434929B2

(12) United States Patent  
Jarvinen et al.

(10) Patent No.: US 9,434,929 B2  
(45) Date of Patent: Sep. 6, 2016

(54) ESTERASES USEFUL IN THE TREATMENT OF CELLULOSIC AND LIGNOCELLULOSIC MATERIAL

(71) Applicant: Roal Oy, Rajamäki (FI)

(72) Inventors: Kristiina Jarvinen, Espoo (FI); Kari Juntunen, Espoo (FI); Taija Leinonen, Riihimäki (FI); Alexandra Komander, Darmstadt (DE); Kim Langfelder, Darmstadt (DE); Jari Vehmaanpera, Klaukkala (FI); Terhi Puranen, Nurmijärvi (FI)

(73) Assignee: Roal Oy (FI)

( * ) Notice: Subject to any disclaimer, the term of this patent is extended or adjusted under 35 U.S.C. 154(b) by 0 days.

(21) Appl. No.: 14/060,999

(22) Filed: Oct. 23, 2013

(65) Prior Publication Data

US 2014/0120586 A1 May 1, 2014

Related U.S. Application Data

(60) Provisional application No. 61/718,992, filed on Oct. 26, 2012.

(51) Int. Cl.
| | |
|---|---|
| *C12N 9/18* | (2006.01) |
| *C12P 19/02* | (2006.01) |
| *C12R 1/19* | (2006.01) |
| *A21D 8/04* | (2006.01) |
| *A23L 1/03* | (2006.01) |
| *C11D 3/386* | (2006.01) |

(52) U.S. Cl.
CPC ............... *C12N 9/18* (2013.01); *A21D 8/042* (2013.01); *A23K 20/189* (2016.05); *A23L 1/034* (2013.01); *C11D 3/38636* (2013.01); *C12P 19/02* (2013.01); *C12R 1/19* (2013.01); *C12Y 301/01073* (2013.01); *Y02P 20/52* (2015.11)

(58) Field of Classification Search
CPC ............................................. C12Y 301/01073
See application file for complete search history.

(56) References Cited

U.S. PATENT DOCUMENTS

| | | | |
|---|---|---|---|
| 3,664,961 A | 5/1972 | Norris | |
| 5,443,750 A | 8/1995 | Convents et al. | |
| 6,143,543 A | 11/2000 | Michelsen et al. | |
| 7,998,713 B2 | 8/2011 | Dunson, Jr. et al. | |
| 8,034,995 B2* | 10/2011 | Maranta et al. | 800/288 |
| 2008/0032344 A1 | 2/2008 | Fallavollita | |
| 2009/0151026 A1 | 6/2009 | Maranta et al. | |
| 2010/0122380 A1 | 5/2010 | Brown et al. | |
| 2012/0036599 A1 | 2/2012 | Gusakov et al. | |

FOREIGN PATENT DOCUMENTS

| | | |
|---|---|---|
| CN | 101228921 A | 7/2008 |
| WO | 94/07998 A1 | 4/1994 |
| WO | 2007/071818 A1 | 6/2007 |
| WO | 2009/146464 A2 | 12/2009 |
| WO | 2011/080317 A2 | 7/2011 |
| WO | 2011/091260 A2 | 7/2011 |
| WO | 2011/161459 A1 | 12/2011 |
| WO | 2012/027282 A2 | 3/2012 |
| WO | 2012/078741 A2 | 6/2012 |
| WO | 2012/134626 A2 | 10/2012 |

OTHER PUBLICATIONS

Amlacher et al. Jul. 22, 2011; Insight into structure and assembly of the nuclear pore complex by utilizing the genome of a eukaryotic thermophile. Cell. 146(2): 277-289; Alignments Only being sent to Applicants.*
Jiang et al. Oct. 2011; Molecular cloning of a ferulic esterase gene from *Chaetomium* sp CQ31 in Pichia pastoris. EMBL: AFU88756.1; Alignments Only being sent to Applicants.*
Fazary et al. 2008; the large-scale use of feryloyl esterases in industry. Biotechnology and Molecular Biology Reveiws 3(5): 95-110.*
Stoesser et al. 2002; The EMBL nucleotide sequence database. Nucleic Acids Research 30(1): 21-26.*
European Nucleotide Archive. downloaded Aug. 19, 2015; www.ebi.ac.uk/ena/about/data-availability-policy.*
J. D. Bendtsen et al., "Improve Prediction of Signal Peptides: SignalP 3.0," J. Mol. Biol. (2004) 340, pp. 783-795.
Donald M. Coen., "The Polymerase Chain Reaction," Current Protocols in Molecular Biology (2001) 15.0.1-15.0.3.
J. A. Donaghy et al., "Novel screening assay for the detection of phenolic acid esterases," World Journal of Microbiology & Biotechnology 10, 41-44.
J. Donaghy et al., "Detection of ferulic acid esterase production by *Bacillus* spp. and lactobacilli," Appl Microbiol Biotechnol (1998) 50: 257-260.
Gerd Gellissen., "Production of Recombinant Proteins. Novel Microbial and Eukaryotic Expression Systems," Wiley-VCH Verlag GmbH & Co. KGaA, ISBN: 3-527-31036-3.
V. V. Joutsjoki et al., "Transformation of Trichoderma reesei with the Hormoconis resinae glucoamylase P (gamP) gene: production of a heterologous glucoamylase by Trichoderma reesei," Curr Genet (1993) 24: 223-228.
T. Karhunen et al., "High frequency one-step gene replacement in Trichoderma reesei. I. Endoglucanase I overproduction," Mol Gen Genet (1993) 241: 515-522.
S. Kühnel et al., "The ferulic acid esterases of Chrysosporium lucknowense C1: Purification, characterization and their potential application in biorefinery," Enzyme and Microbial Technology 50(2012) 77-85.

(Continued)

*Primary Examiner* — Karen Cochrane Carlson
(74) *Attorney, Agent, or Firm* — Banner & Witcoff, Ltd.

(57) ABSTRACT

The present invention discloses novel polypeptides and enzyme preparations containing them, which improve the efficiency of cellulose and lignocellulose degradation even at elevated temperatures. The polypeptides can be produced using conventional recombinant DNA technologies. The related polynucleotides, vectors and host cells are also disclosed. The polypeptides and the enzyme preparations containing them are particularly useful in improving the efficiency of cellulose and lignocellulose degradation, in improving the quality of animal feed, in machine dishwashing applications, in detergent compositions, in pulp and paper, textile, food, baking or beverage industry.

2 Claims, 2 Drawing Sheets

(56) References Cited

OTHER PUBLICATIONS

S. B. Needleman et al., "A General Method Applicable to the Search for Similarities in the Amino Acid Sequence of Two Proteins," J. Mol. Biol. (1970) 48, 443-453.

H. Nielsen et al., "Identification of prokaryotic and eukaryotic signal peptides and prediction of their cleavage sites," Protein Engineering vol. 10 No. 1 pp. 1-6, 1997.

H. Nielsen et al., "Prediction of signal peptides and signal anchors by a hidden Markov model," In: Proceedings of the Sixth International Conference on Intelligent Systems for Molecular Biology (ISMB 6), AAAI Press, Menlo Park, California, pp. 122-130.

M. Paloheimo et al., "High-Yield Production of a Bacterial Xylanase in the Fliamentous Fungus Trichoderma reesei Requires a Carrier Polypeptide with an Intact Domain Structure," Applied and Environmental Microbiology, Dec. 2003, p. 7073-7082, vol. 69, No. 12.

M. Penttila et al., "A versatile transformation system for the cellulolytic filamentous fungus Trichoderma reesei," Gene, 61 (1987) 155-164.

M. Poutanen et al., "Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis," Rapid Commun. Mass Spectrum. 2001; 15: 1685-1692.

U. Raeder et al., "Rapid preparation of DNA from filamentous fungi," Letters in Applied Microbiology 1985, 1, 17-20.

A. Shevchenko et al., "Mass Spectrometric Sequencing of Proteins from Silver-Stained Polyacrylamide Gels," Anal. Chem. 1996, 68, 850-858.

F.J. Short et al., "Determination of titanium dioxide added as an inert marker in chicken digestibility studies," Animal Feed Science Technology 59 (1996) 215-221.

H. Visser et al., "Development of a mature fungal technology and production platform for industrial enzymes based on a Myceliophthora thermophila isolate, previoulsy known as Chrysosporium luchnowense C1," Jun. 2011, Industrial Biotechology 7: 214-223.

International Search Report received in corresponding Finnish Application No. 20126115 mailed Aug. 12, 2013.

Sequence Listing ID No. 137 from WO 2012/134626 and 11; Rundate: Aug. 7, 2013.

Sequence Listing ID No. 170 from WO 2012/027282 and 11; Rundate: Aug. 7, 2013.

Sequence Listing ID No. 2 from WO 2012/078741 and 11; Rundate: Aug. 7, 2013.

Sequence Listing ID No. 75 from WO 2009/146464 and 11; Rundate: Aug. 7, 2013.

\* cited by examiner

ESTERASES USEFUL IN THE TREATMENT OF CELLULOSIC AND LIGNOCELLULOSIC MATERIAL

FIELD OF THE INVENTION

The present invention relates to novel polypeptides and enzyme preparations containing them, which are useful in various industrial applications even at elevated temperatures. The polypeptides and the enzyme preparations containing them are particularly useful in improving the efficiency of cellulose and lignocellulose degradation, in improving the quality of animal feed, in machine dishwashing applications, in detergent compositions, in pulp and paper, textile, food, baking or beverage industry. The invention also relates to polynucleotides, vectors and host cells comprising the polynucleotides as well as methods of producing the polypeptides.

BACKGROUND OF THE INVENTION

Most of the carbohydrates in plants are in the form of lignocellulose, which essentially consists of cellulose, hemicellulose, and pectin. Cellulose is the major structural component of higher plants. Hemicellulose is a heterogeneous group of carbohydrate polymers containing mainly different glucans, xylans and mannans Pectin consists of a complex set of polysaccharides that are present in most primary cell walls.

Cellulosic material i.e. material comprising cellulose, hemicellulose and/or lignocellulose is degraded in nature by a number of various organisms including bacteria and fungi which produce enzymes capable of hydrolyzing carbohydrate polymers. Degradation usually requires different cellulases acting sequentially or simultaneously. Degradation of more complex cellulose containing substrates requires a broad range of various enzymes.

Lignocellulose can be converted into bioethanol and other chemical products via fermentation following hydrolysis to fermentable sugars. In a conventional lignocellulose-to-ethanol process the lignocellulosic material is first pretreated either chemically or physically to make the cellulose fraction more accessible to hydrolysis. Thereafter the cellulose fraction is hydrolysed to obtain sugars that can be fermented by yeast or other fermentative organisms into ethanol and distilled to obtain pure ethanol. Lignin is obtained as a main co-product that may be used as a solid fuel.

Methods for processing of lignocellulosic biomass have been brought out in U.S. Pat. No. 7,998,713, which discloses a process involving pretreatment of biomass with ammonia. Following pretreatment, the biomass is treated with a saccharification enzyme consortium, i.e. cellulose-hydrolyzing glycosidases, to produce fermentable sugars. The sugars are then contacted with a microorganism that can ferment the sugars and produce ethanol. US20080032344 discloses a process for treating biomass to separately recover holocellulose and near-native lignin therefrom whereby the lignin and holocellulose-derived sugars can then be subjected to different treatments to produce fuels, chemicals, and/or new materials.

Processing of biomass by lignocellulolytic enzymes has significant potential applications in biofuel, starch, textile, detergent, pulp and paper, food, feed or beverage industry. In many of these applications xylanases are used in connection with various other lignocellulolytic enzymes. In paper and pulp industry xylanases are used in papermaking to reduce chlorine consumption and toxic discharge during bleaching of wood pulp, in textile processing to reduce or replace chemical retting, in bioremediation/bioconversion to treat/recycle wastes and to produce biofuels and fine chemicals and in baking to improve the elasticity and stability of dough or the volume and anti-staling properties of the baked product. WO2011091260 discloses compositions and methods for treating lignocellulosic material with a dual activity enzyme having xylanase and cellulase activity. The enzyme is stable and active at increased pH and increased temperatures. US20120036599 discloses novel fungal enzymes isolated from *Chrysosporium lucknowense* C1 (now reindentified as *Myceliophthora thermophile*; Visser et al., 2011) suitable for biomass processes, detergent processes, deinking and biobleaching of pulp and paper and treatment of waste streams.

Enzymes degrading hemicellulose, such as hemicellulases, xylanases, pectinases and esterases have been used to improve the break-down of plant cell walls e.g. in animal feed compositions. Especially ferulic acid esterases have been observed to act synergistically with xylanase to release ferulic acid from plant cell walls. CN101228921 discloses a composition of ferulic acid esterase, cellulase, xylanase and dextranase for feed stuff, which enzymatically improves release of sugar from animal feed. U.S. Pat. No. 6,143,543 discloses an enzyme obtainable from *Aspergillus* and having ferulic acid esterase activity, which is useful for preparing food and animal feed. Polypeptides from *Humicola insolens* having feroyl esterase activity are disclosed in US20090151026. Kühnel et al. 2012 disclose ferulic acid esterases of *Chrysosporium lucknowense* C1, which are most active at neutral pH and temperatures up to 45° C.

The cost and hydrolytic efficiency of the enzymes are the major factors that restrict the extensive use of biological hydrolysis processes for biomass conversion. The hydrolytic efficiency of enzyme complexes in the process of lignocellulose saccharification depends both on properties of the individual enzymes and the ratio of each enzyme within the complex. In addition to improving characteristics with respect to individual enzymes in the enzyme complex it is beneficial to improve the enzymatic degradation of cellulosic material by influencing on the activity of cellulases. Furthermore, optimization of the components in enzyme complexes and supplementation of synergistically acting enzymes are needed to improve hydrolytic efficiency.

Hence, there is still a continuous need for new efficient methods of degrading cellulosic substrates, in particular lignocellulosic substrates, and for inexpensive enzymes and enzyme mixtures, which can considerably improve the enzymatic degradation of cellulosic material and also reduce the required enzyme dosage. Moreover, there is a need for processes which work not only at moderate temperatures but also at high temperatures, thus increasing the reaction rates and enabling the use of high biomass consistency leading to high sugar and ethanol concentrations. Because of environmental concerns and consumer demands, alternative enzyme-aided technologies have been desired. Furthermore, there is a need for enzymes and processes, which can be used in a variety of agricultural and industrial applications and which allow the design of more flexible process configurations.

The present invention aims to meet at least part of these needs.

BRIEF DESCRIPTION OF THE INVENTION

It is an object of the present invention to provide novel polypeptides and enzyme preparations containing them, which are useful in various industrial applications even at elevated temperatures. Especially the object of the invention is to provide polypeptides that are particularly useful in improving the efficiency of cellulose and lignocellulose degradation, in improving the quality of animal feed, in machine dishwashing applications, in detergent compositions, in pulp and paper, textile, food, baking or beverage industry.

The objects of the invention are achieved by novel ferulic acid esterases obtained from *Chaetomium thermophilum* or *Melanocarpus albomyces*.

The present invention provides a ferulic acid esterase comprising an amino acid sequence having at least 76% sequence identity to SEQ ID NO: 11, or at least 73% sequence identity to SEQ ID NO:12, or a fragment or variant thereof having ferulic acid esterase activity.

The present invention also relates to an isolated polynucleotide selected from the group consisting of:
 a) a polynucleotide comprising the coding sequence as shown in SEQ ID NO: 9 or 10;
 b) a polynucleotide encoding a polypeptide of claim 1;
 c) a polynucleotide encoding a fragment of a polypeptide encoded by a polynucleotide of a) or b), wherein said fragment is having ferulic acid esterase activity; and
 d) a polynucleotide comprising a nucleotide sequence which is degenerate to the nucleotide sequence of a polynucleotide sequence of a) or b);
 or the complementary strand of such a polynucleotide.

The invention is also directed to a vector, which comprises said polynucleotide and a host cell comprising said vector. *Escherichia coli* strains having accession number DSM 26070 and DSM 26071 are also included in the invention.

The invention provides a method of producing said ferulic acid esterase polypeptide, the method comprising the steps of transforming a host cell with an expression vector encoding said polypeptide, and culturing said host cell under conditions enabling expression of said polypeptide, and optionally recovering and purifying said polypeptide.

The invention also provides enzyme preparations comprising at least one of the novel ferulic acid esterases and the use of said enzyme preparation for biomass processing, preferably in biofuel, starch, textile, detergent, pulp and paper, food, baking, feed or beverage industry.

The enzyme preparation of the invention has a great potential in the pulp and paper industry, for instance, in deinking to release ink from fiber surfaces, in improving pulp drainage, for better runability of the paper machine and fiber modification for all types of pulp and paper products.

The invention also provides a method for treating cellulosic and lignocellulosic material with a ferulic acid esterase or an enzyme preparation comprising said esterase, wherein the method comprises reacting the fibrous/cellulosic material with said polypeptide or enzyme preparation comprising said polypeptide.

In one aspect the present invention relates to a method for improving fabric care properties or textile cleaning effect of a detergent composition, comprising adding a ferulic acid esterase of the invention to the detergent composition.

The present invention also provides a detergent composition comprising the ferulic acid esterase and relates to a method for improving fabric care properties or textile cleaning effect of a detergent composition, comprising adding a ferulic acid esterase of the invention to the detergent composition.

In one aspect the invention provides an animal feed comprising the novel ferulic acid esterase polypeptide. The animal feed as such may be used to improve animal growth rate and feed conversion ratio.

Specific embodiments of the invention are set forth in the dependent claims. Other objects, details and advantages of the present invention will become apparent from the following drawings, detailed description and examples.

The present inventors found that the novel ferulic acid esterases and methods of the invention offer considerable potential to increase the overall performance of cellulase enzyme mixtures and reduce protein loading required achieving effective degradation of lignocellulosic substrates. The novel ferulic acid esterases are applicable in degrading different cellulosic and lignocellulosic materials particularly in combination with enzymes, such as cellulases and/or xylanases, used in degradation of various cellulosic or lignocellulosic materials. The novel ferulic acid esterases of the invention are effective in reducing fibrous/cellulosic fibres typically found in the filter of the dishwashing machine. The inventors further noticed that novel ferulic acid esterases are beneficial for improving the quality of animal feed whereby plant material is treated with the enzymes. Moreover, treating cellulosic and lignocellulosic material with a ferulic acid esterase or an enzyme preparation comprising said esterase is beneficial for removing lignin's brown color and tendency to reduce the strength of the paper product and thus improve the paper making properties of the fibers.

The present inventors also found that the novel ferulic acid esterases are very effective over a broad range of temperatures, and although they improve efficiency of cellulolytic enzymes at standard hydrolysis temperatures, they are also very efficient at high temperatures. This makes them extremely well suited for varying cellulosic substrate hydrolysis processes carried out both at conventional temperatures and at elevated temperatures. In the conventional separate hydrolysis and fermentation process (SHF) the temperature of enzymatic hydrolysis is typically higher than that of fermentation. The use of thermostable enzymes in the hydrolysis offer potential benefits, such as higher reaction rates at elevated temperatures, reduction of enzyme load due to higher specific activity and stability of enzymes, increased flexibility with respect to process configuration and decreased contamination risk. The general robustness of the thermostable enzymes compared to mesophilic ones also increases the recyclability of enzymes in the industrial process. Overall the present invention may lead to significant savings in energy and investment costs.

BRIEF DESCRIPTION OF THE DRAWINGS

In the following the invention will be described in greater detail by means of preferred embodiments with reference to the attached drawings.

DETAILED DESCRIPTION OF THE INVENTION

Figure 1:
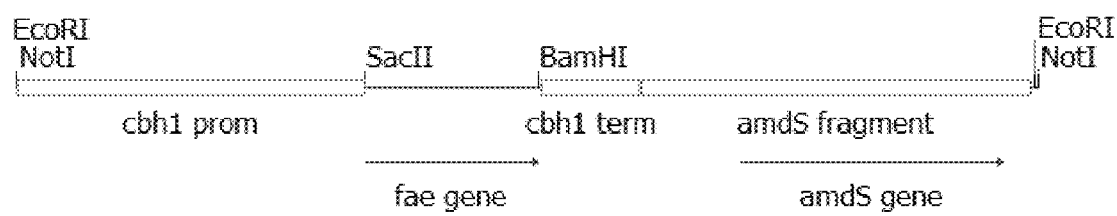
FIG. 1 schematically shows the cassette used for expressing the fae genes in *Trichoderma reesei*. The fae genes were under the control of *T. reesei* cbh1/cel7A promoter (cbh1 prom) and the termination of the transcription was ensured by using *T. reesei* cbh1/cel7A terminator sequence (cbh1 term). The amdS gene was included as a transformation marker.

Cellulose is the major structural component of higher plants. It provides plant cells with high tensile strength helping them to resist mechanical stress and osmotic pressure. Cellulose is a β-1,4-glucan composed of linear chains of glucose residues joined by β-1,4-glycosidic linkages. Cellobiose is the smallest repeating unit of cellulose. In cell walls cellulose is packed in variously oriented sheets, which are embedded in a matrix of hemicellulose and lignin.

Hemicellulose is a heterogeneous group of carbohydrate polymers containing mainly different glucans, xylans and mannans. Hemicellulose consists of a linear backbone with β-1,4-linked residues substituted with short side chains usually containing acetyl, glucuronyl, arabinosyl and galactosyl. Hemicellulose can be chemically cross-linked to lignin. Lignin is a complex cross-linked polymer of variously substituted p-hydroxyphenylpropane units that provides strength to the cell wall to withstand mechanical stress, and it also protects cellulose from enzymatic hydrolysis.

"Cellulose" or "cellulosic material" as used herein, relates to any material comprising cellulose, hemicellulose and/or lignocellulose as a significant component. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue. Examples of cellulosic material include textile fibers derived e.g. from cotton, flax, hemp, jute and the man-made cellulosic fibers as modal, viscose and lyocel. Examples of cellulosic material also include fibrous or cellulosic type residues like soils found in a filter of automatic dishwashers.

"Lignocellulose" is a combination of cellulose and hemicellulose and lignin. It is physically hard, dense, and inaccessible and the most abundant biochemical material in the biosphere. "Biomass" or "lignocellulosic material" means any material comprising lignocellulose. Such materials are for example: hardwood and softwood chips, wood pulp, sawdust and forestry and wood industrial waste, agricultural biomass as cereal straws, sugar beet pulp, corn fibre, corn stover and cobs, sugar cane bagasse, stems, leaves, hulls, husks, and the like; waste products as municipal solid waste, newspaper and waste office paper, milling waste of e.g. grains; dedicated energy crops (e.g., willow, poplar, swithcgrass or reed canarygrass, and the like). Preferred examples are corn fibre, corn stover, switchgrass, cereal straw, sugarcane bagasse and wood derived materials.

Cellulosic material is degraded in nature by a number of various organisms including bacteria and fungi which produce enzymes capable of hydrolyzing carbohydrate polymers. Degradation usually requires different cellulases acting sequentially or simultaneously. Degradation of more complex cellulose containing substrates requires a broad range of various enzymes. For the degradation process the cellulosic material may be used as is or may be subjected to pretreatment, using conventional methods known in the art.

"Cellulolytic enzymes" or "cellulases" are enzymes having "cellulolytic activity", which means that they are capable of hydrolysing cellulosic substrates or derivatives thereof into smaller saccharides. Cellulolytic enzymes thus include both cellulases and hemicellulases. Cellulases as used herein include (1) endoglucanases (EG, EC 3.2.1.4) which cut internal beta-1,4-glucosidic bonds; (2) exoglucanases or cellobiohydrolases (CBH, EC 3.2.1.176, EC 3.2.1.91) that cut the dissaccharide cellobiose from the reducing or non-reducing end of the crystalline cellulose polymer chain; (3) beta-1,4-glucosidases (BG, EC 3.2.1.21) which hydrolyze the cellobiose and other short cello-oligosaccharides to glucose.

"Hemicellulases", are enzymes hydrolysing hemicellulose. Hemicellulases include both endo-acting and exo-acting enzymes, such as xylanases, β-xylosidases, galactanases, α-galactosidases, β-galactosidases, endo-arabinases, arabinofuranosidases, mannanases and β-mannosidases.

"Xylanases" are enzymes that hydrolyze the β-1,4 bond in the xylan backbone, producing short xylo-oligosaccharides. The degradation of the xylan backbone depends on two classes of enzymes: endoxylanases and β-xylosidases. Endoxylanases (EC 3.2.1.8) cleave the xylan backbone into smaller oligosaccharides, which can be further degraded to xylose by β-xylosidases (EC 3.2.1.37). Other enzymes involved in the degradation of xylan include, for example, acetylxylan esterase, arabinase, alpha-glucuronidase, ferulic acid esterase, and p-coumaric acid esterase.

"Ferulic acid esterases" (FAEs) (EC 3.1.1.73) are a class of enzymes that are able to hydrolyze ester linkages of ferulic acid and diferulic acid present in plant cell walls. Ferulic acid is involved in crosslinking xylan chains of the hemicellulose together or xylan to lignin. Specifically, the ferulic acid esterases have 4-hydroxy-3-methoxycinnamoyl-sugar hydrolase activity that catalyzes the hydrolysis of the 4-hydroxy-3-methoxycinnamoyl (feruloyl) group from an esterified sugar, to produce ferulate (4-hydroxy-3-methoxycinnamate). Several studies indicate that ferulic acid esterases are alpha/beta hydrolases with a serine, histidine, and aspartic acid catalytic triad. Ferulic acid esterase is also known e.g. as feruloyl esterase, cinnamoyl esterase, cinnamic acid esterase, hydroxycinnamoyl esterase. FAEs are classified into four subgroups (A, B, C, and D) according to their activities toward synthetic substrates and dehydrodiferulic acids. In the present invention the FAEs are preferably of B-type esterases. Type B ferulic acid esterases release ferulic acid-ester linked to either C-2 of feruloylated arabinose or C-6 feruloylated galactose residues The present invention is based on studies, which attempted to find novel polypeptides which would improve the efficiency of cellulose and lignocellulose degradation and which could be used for versatile applications even at elevated temperatures. Two novel ferulic acid esterases referred to as Ct_FAE and Ma_FAE were obtained (Table 1).

TABLE 1

The ferulic acid esterases genes and polypeptides of the invention

| Gene | nucleic acid SEQ ID NO: | Protein | No of aas | amino acid SEQ ID NO: |
|---|---|---|---|---|
| Ct_fae | 9 | Ct_FAE | 289 | 11 |
| Ma_fae | 10 | Ma_FAE | 271 | 12 |

The novel ferulic acid esterases according to the present invention are obtainable from *Chaetomium thermophilum* or *Melanocarpus albomyces*. Preferably the polypeptides are obtainable from *Chaetomium thermophilum* strain having the characteristics of strain ALKO4265 deposited as CBS 132416 or *Melanocarpus albomyces* strain having the characteristics of strain ALKO4237 deposited as CBS 132099. "Obtainable from" means that they can be obtained from said species, but it does not exclude the possibility of obtaining them from other sources. In other words they may originate from any organism including plants. Preferably they originate from microorganisms e.g. bacteria or fungi. The bacteria may be for example from a genus selected from *Bacillus*, *Azospirillum* and *Streptomyces*. More preferably the enzyme originates from fungi (including filamentous fungi and yeasts), for example from a genus selected from the group consisting of *Thermoascus*, *Acremonium*, *Chaetomium*, *Achaetomium*, *Thielavia*, *Aspergillus*, *Botrytis*, *Chrysosporium*, *Collybia*, *Fomes*, *Fusarium*, *Humicola*, *Hypocrea*, *Lentinus*, *Melanocarpus*, *Myceliophthora*, *Myriococcum*, *Neurospora*, *Penicillium*, *Phanerochaete*, *Phlebia*, *Pleurotus*, *Podospora*, *Polyporus*, *Rhizoctonia*, *Scytalidium*, *Pycnoporus*, *Talaromyces*, *Trametes* and *Trichoderma*.

The novel ferulic acid esterases of the invention preferably comprise an amino acid sequence having at least 76% sequence identity to SEQ ID NO: 11, or at least 73% sequence identity to SEQ ID NO: 12, or a fragment or variant thereof having ferulic acid esterase activity. According to one embodiment of the invention, the polypeptide has at least 77, 78, 79, 80, 85, 90, 95, 98 or 99% identity to SEQ ID NO: 11 or at least 74, 75, 80, 85, 90, 95, 98 or 99% SEQ ID NO: 12 or to a fragment thereof having ferulic acid esterase activity.

By the term "identity" is here meant the global identity between two amino acid sequences compared to each other from the first amino acid encoded by the corresponding gene to the last amino acid. The identity of the full-length sequences is measured by using EMBOSS Needle Needleman-Wunsch global alignment program at EBI (European Bioinformatics Institute) http://www.ebi.ac.uk/Tools/psa/emboss_needle/with the following parameters: BLOSUM62, Gap open 10, Gap extend 0.5. The algorithm is described in Needleman and Wunsch (1970). The man skilled in the art is aware of the fact that results using Needleman-Wunsch algorithm are comparable only when aligning corresponding domains of the sequence and using the same parameters in each comparison. Consequently comparison of e.g. cellulase sequences including cellulose binding module (CBM) or signal sequences with sequences lacking those elements cannot be done.

By the term "fragment having ferulic acid esterase activity" is meant any fragment of a defined sequence that has capability to improve the efficiency of cellulose and lignocellulose degradation catalyzed by an enzyme having ferulic acid esterase activity. In other words a fragment improving degradation of cellulosic material may be the mature protein part of the defined sequence, or it may be only a fragment of the mature protein part, provided that it still has capability to improve cellulose and lignocellulose degradation by hydrolyzing the ester linkages and releasing ferulic acid.

For purposes of the present invention, the improvement of lignocellulose degradation is determined by measuring the increase of the total xylose concentration from the hydrolysis of cellulosic and lignocellulosic materials by a cellulolytic enzyme mixture containing the ferulic acid esterase compared to equal protein loading without the ferulic acid esterase. For the purpose of cleaning of the interior of dishwashing machine, the performance of ferulic acid esterase is determined by measuring the fiber residues left after the treatment with a cellulolytic enzyme mixture containing the ferulic acid esterase compared to equal protein loading of the cellulolytic enzyme mixture without the ferulic acid esterase. For the feed purposes the efficacy of the ferulic acid esterase, is determined by improvements in animal growth rate and feed conversion ratio.

The novel ferulic acid esterase polypeptides may also be variants of said polypeptides. A "variant" may be a polypeptide that occurs naturally e.g. as an allelic variant within the same strain, species or genus, or it may have been generated by mutagenesis. It may comprise amino acid substitutions, deletions or insertions, but it still functions in a substantially similar manner to the polypeptides defined above i.e. it comprises a fragment having ferulic acid esterase activity.

The ferulic acid esterases are usually produced in the cell as prepolypeptides comprising a signal sequence that is cleaved off during secretion of the protein. They may also be further processed during secretion both at the N-terminal and/or C-terminal end to give a mature, enzymatically active protein. A fragment having ferulic acid activity denotes that the polypeptide may be either in immature or mature form, preferably it is in mature form, i.e. the processing has taken place. In addition, the "mature form" means an enzyme which has been cleaved from its carrier protein in fusion constructions.

The ferulic acid esterase polypeptides of the present invention are preferably recombinant proteins, which may be produced in a generally known manner. A polynucleotide fragment of the ferulic acid esterase gene is isolated, the gene is inserted under a strong promoter into an expression vector, the vector is transformed into suitable host cells and the host cells are cultivated under conditions provoking production of the enzyme. Methods for protein production by recombinant technology in different host systems are well known in the art (Sambrook and Russel, 2001; Coen, 2001; Gellissen, 2005). Preferably the polypeptides are produced as extracellular proteins that are secreted into the culture medium, from which they can easily be recovered and isolated.

The recombinant polypeptide may be a fused polypeptide in which another polypeptide is fused at the N-terminus or the C-terminus of the polypeptide. Techniques for producing fusion polypeptides are known in the art, and include ligating the coding sequences encoding the polypeptides so that they are in frame and that expression of the fused polypeptide is under control of the same promoter and terminator.

The present invention relates to novel polynucleotides which comprise a nucleotide sequence of SEQ ID NO: 9 or 10, or a sequence encoding a novel polypeptide as defined above, including complementary strands thereof. "Polynucleotide" as used herein refers to both RNA and DNA, and it may be single stranded or double stranded. Further the polynucleotide may be degenerate as a result of the genetic code to any one of the sequences as defined above. This means that different codons may code for the same amino acid.

The polynucleotide may also be a fragment of said polynucleotides comprising at least 20 nucleotides. According to one embodiment of the invention the polynucleotide has a sequence set forth as SEQ ID NO: 5, 6, 7 or 8.

According to another embodiment of the invention, the polynucleotide comprises a gene similar to that included in a microorganism having accession number DSM 26070 or DSM 26071.

The present invention relates to a recombinant expression "vector" comprising a polynucleotide encoding the ferulic acid esterase polypeptide as characterized above, operably linked to regulatory sequences, which are capable of directing the expression of a gene encoding said ferulic acid esterase polypeptide in a suitable host. Said regulatory sequences may be homologous or heterologous to the production organism or they may originate from the organism, from which the gene encoding the ferulic acid esterase polypeptide of the invention is isolated. The expression vector may further comprise marker genes for selection of the transformant strains or the selection marker may be introduced to the host in another vector construct by co-transformation.

Still the present invention relates to a production "host", which can be any homologous or heterologous organism capable of expressing the desired polypeptide. Preferably the host is a microbial cell, more preferably a fungus. Most preferably the host is a filamentous fungus. Preferred hosts for producing the polypeptides of the invention are in particular strains from the genus *Trichoderma* or *Aspergillus*. Preferably the recombinant host is modified to express and secrete cellulolytic enzymes or polypeptides of the invention as its main activity or one of its main activities. This can be done by deleting genes encoding major homologous secreted enzymes e.g. the four major cellulases of *Trichoderma* and by integrating heterologous genes to a locus with high expression and production levels.

The present invention relates also to a method for producing a ferulic acid esterase polypeptide of the invention, said method comprising the steps of transforming a host cell with an expression vector encoding said polypeptide, and culturing said host cell under conditions enabling expression of said polypeptide, and optionally recovering and purifying said polypeptide. The production medium may be a medium suitable for growing the host organism and containing inducers for efficient expression.

The polypeptides of the present invention may be isolated, which in the present context may simply mean that the cells and cell debris have been removed from the culture medium containing the polypeptide. Conveniently the polypeptides are isolated e.g. by adding anionic and/or cationic polymers (flocculants) to the spent culture medium to enhance precipitation of cells and cell debris. The medium is then filtrated using an inorganic filtering agent and a filter to remove the precipitants formed. After this the filtrate is further processed using a semi-permeable membrane to remove excess of salts, sugars and metabolic products. The polypeptides can also be purified or concentrated by crystallization.

The novel ferulic acid esterases which are obtainable by the method of the present invention may be components of an enzyme preparation. The term "enzyme preparation" denotes to a composition comprising at least one of the novel ferulic acid esterases described herein. The ferulic acid esterases in the enzyme preparation may be a recombinant ferulic acid esterase protein comprising an amino acid sequence having at least 76% sequence identity to SEQ ID NO: 11 or at least 73% sequence identity to SEQ ID NO: 12 or a fragment or variant thereof having ferulic acid esterase activity. According to one embodiment of the invention the enzyme preparation comprises a polypeptide having at least 77, 78, 79, 80, 85, 90, 95, 98 or 99% identity to SEQ ID NO: 11 or at least 74, 75, 80, 85, 90, 95, 98 or 99% identity to SEQ ID NO:12.

The enzyme preparation may comprise a ferulic acid esterase of the invention as the major enzymatic component. Alternatively, the enzyme preparation may further comprise at least one enzyme selected from a group of cellobiohydrolase, endoglucanase, beta-glucosidase, beta-glucanase, xyloglucanase, xylanase, beta-xylosidase, cellobiose dehydrogenase, mannanase, beta-mannosidase, α-glucuronidase, acetyl xylan esterase, α-arabinofuranosidase, α-galactosidase, pectinase, involving endo- and exo-α-L-arabinases, endo- and exo-galactoronase, endopectinlyase, pectate lyase and pectinesterase, phenol esterase, ligninase involving lignin peroxidase, manganese-dependent peroxidase, $H_2O_2$-generating enzyme, laminarinase, chitosanase, GH61 protein and laccase with or without mediators. The enzyme preparation may contain any combination of these enzymes and ferulic acid esterases of the invention, but the enzymes are not limited to those described herein. They can for example also be commercially available enzyme preparations.

Preferably the enzyme preparation of the invention comprises a ferulic acid esterase in combination with xylanase and optionally cellobiohydrolase, endoglucanase and/or beta-glucosidase. Most preferably the enzyme preparation comprises a ferulic acid esterase in combination with xylanase. Different mixtures of ferulic acid esterases and xylanases or ferulic acid esterases and cellulolytic enzymes may be used to suit different process conditions.

In addition to the ferulic acid esterases, the enzyme preparation of the invention may contain additives, such as mediators, stabilizers, buffers, preservatives, surfactants and/or culture medium components. Preferred additives are such, which are commonly used in the enzyme preparations intended for a particular application. The enzyme preparations of the invention may also contain metal and/or redox-active cofactors.

The enzyme preparation may be in the form of liquid, powder or granulate. It may be a filtrate containing one or more cellulolytic enzymes. Preferably the enzyme preparation is a spent culture medium. "Spent culture medium" refers to the culture medium of the host comprising the produced enzymes/polypeptides. Preferably the host cells are separated from the said medium after the production. The enzyme preparation or composition may also be a "whole culture broth" obtained, optionally after inactivating the production host(s) or microorganism(s) without any biomass separation, down-stream processing or purification of the desired cellulolytic enzyme(s). In the consolidated bioprocess the enzyme composition or at least some of the enzymes of the enzyme composition may be produced by the fermentative microorganism.

The enzyme preparation may contain the polypeptides in at least partially purified and isolated form. The culture medium with or without host cells may be utilized as an enzyme preparation as such without further purification, because the ferulic acid esterase proteins can be secreted into the culture medium, and they display activity in the ambient conditions of the spent culture medium.

The ferulic acid esterases of the invention perform well at moderate to elevated temperatures. The term "moderate temperature" or "conventional temperature" in context of the present invention means temperature ranges from about 30° C. to 45° C. The term "elevated temperature" or "high temperature" refers to temperature ranges from about 45° C. to 70° C. Enzymes active or stable at such elevated temperature ranges are also called "thermostable" or "thermophilic" enzymes. The ferulic acid esterases of the invention are used preferably at temperatures between about 35° C. and about 60° C. More preferably they are used at temperatures between 37° C. and 60° C., most preferably at temperatures between 45° C. and 60° C.

The present invention provides a method for treating cellulosic or lignocellulosic material, wherein the cellulosic or lignocellulosic material is reacted with an effective amount of the ferulic acid esterase polypeptide or the enzyme preparation comprising said polypeptide in the presence of cellulolytic enzymes under suitable conditions, such as appropriate pH and temperature, and the reaction is allowed to continue for a time sufficient for the enzymatic reaction to take place. The ferulic acid esterase polypeptides improve the activity of cellulolytic enzymes, either in the acid, neutral, or alkaline pH-range.

According to one embodiment of the present invention the method of treating cellulosic material comprises cleaning the interior of a dishwasher by contacting at least part of the interior of the dishwasher with the ferulic acid esterase or the enzyme preparation of the invention. The enzyme preparation may be placed directly into the interior of the machine or alternatively into a dispensing draw or cup of the machine or to areas in the interior of the dishwasher, which require removal of fibrous soils (e.g. the filter). Useful methods for cleaning dishwasher machine are described e.g. in WO2011161459. The enzyme preparation may also be specifically applied to those areas of a dishwasher machine, where fibrous/cellulosic soil is deposited. The method may be applicable manually whilst the dishwasher is not being operated or whilst the dishwasher is undergoing a loaded or unloaded washing and/or rinsing cycle. Moreover, the ferulic acid esterases of the present invention may be used at all wash temperatures of a dishwashing system.

One aspect of the invention relates to a method for improving fabric care properties or textile cleaning effect of a detergent composition, comprising adding a polypeptide or enzyme preparation of the invention to the detergent composition.

According to another embodiment of the present invention the method of treating cellulosic material comprises treating any cellulosic or lignocellulosic material, such as textile material, plants used in animal feed, or wood-derived mechanical or chemical pulp or secondary fiber. The ferulic acid esterases can also be added to wastewater to reduce the amount of solids such as sludge. The invention is also directed for enzymatically treating plant biomass and removing ligning component for pulp and paper industry, typically in pulp bleaching.

In the context of the present invention ferulic acid esterase may function synergistically with other hydrolytic plant cell wall degrading enzymes to facilitate complete or improve degradation of the complex plant cell walls. "Synergistically acting enzyme" is any additional enzyme capable of hydrolyzing lignocellulose or improving or promoting the cellulose degradation wherein the synergistically acting enzyme is typically provided in addition to a core enzyme or core set of enzymes. Synergistically acting enzyme can have the same or similar function or a different function as an enzyme or enzymes in the core set of enzymes. The core enzymes may include cellulolytic enzymes, such as e.g. cellulases, xylanases, ligninases, amylases, lipidases, or glucuronidases. The ferulic acid esterases of the invention "improve the cellulose and lignocellulose degradation" catalyzed by an enzyme having cellulolytic activity. In other words, converting a cellulosic or lignocellulosic material with cellulolytic enzymes in the presence of a ferulic acid esterase increases the degradation of cellulosic or lignocellulosic material compared to the presence of only the cellulolytic enzymes.

Ferulic acid esterases alter the physical properties of the cell walls of plants and make them more accessible for further enzymatic attack by e.g. cellulases and xylanases. Utilizing ferulic acid esterases the productivity of fermentable sugars from lignocellulosic material may be increased. The fermentable sugars may then be fermented by yeast into ethanol, and used as fuel. They can also be used as intermediates or raw materials for the production of various chemicals or building blocks for the processes of chemical industry, e.g. in so called biorefinery. Any method known in the art comprising pretreatment, enzymatic hydrolysis, fermentation, or a combination thereof, can be used in the context of the present invention. Current pretreatments include mechanical, chemical or thermal processes and combinations thereof. The material may for example be pretreated by steam explosion or acid hydrolysis.

The ferulic acid esterases, enzyme preparations and the methods of the invention may be applied in any process involving cellulolytic enzymes, such as biomass processing, and in biofuel, starch, textile, detergent, pulp and paper, food, feed or beverage industry.

The ferulic acid esterases may be used to degrade tough fibrous/cellulosic soils which may otherwise be difficult to remove from the interior of the dishwashing machine such as from the filter. Soils which can be broken down by the ferulic acid esterase or the enzyme preparation of the invention include cereals, fruits and vegetables. Some specific examples include apple and orange peels and wheat fiber.

The ferulic acid esterases and enzyme preparations of the invention may be used in combination with cellulolytic enzymes in papermaking to reduce chlorine consumption and toxic discharge during bleaching of wood pulp and deinking of paper. Furthermore, the ferulic acid esterases may be used in biorefining of pulp for paper making. The amount of ferulic acid esterase or enzyme preparations used for pulp and paper modification typically varies depending upon the material that is used, the pH and temperature of the system, and the retention time.

The ferulic acid esterases of the present invention can be used in detergent compositions in combination with other enzyme activities. They may be used as a detergent additive suitable for laundry detergent and dish wash compositions, including automatic dish washing compositions. A detergent means a substance or material intended to assist cleaning or having cleaning properties. Preferably the ferulic acid esterases of the present invention may be used in an automatic dishwasher cleaning composition.

The ferulic acid esterases and enzyme preparations of the invention are useful in the treatment of textile materials, such as fabrics and garments. The textile material may be manufactured of natural cellulose containing fibers or man-made cellulose containing fibers or mixtures thereof, or a blend of synthetic fibers and cellulose containing fibers. The enzyme preparations of the present invention are especially useful in biofinishing. "Biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability and which may improve also the dyeability. Additional uses further include the use in biostoning of denim. "Biostoning" refers to the enzymatic denim finishing processes in which cellulases have replaced or are being used together with pumice stones to give the fabric its desired "worn" or "abraded" look. Controlled enzyme treatments result in less damage to the garments and machines and eliminate the need for disposal of stones.

The ferulic acid esterases and enzyme preparations of the present invention may also be used in baking to improve the development, elasticity, and/or stability of dough and/or the volume, crumb structure, and/or anti-staling properties of the baked product. Furthermore, they may also be used in the beverage industry, for example for beer brewing to improve filterability, for the preparation of fruit or vegetable juice to increase yield, or for wine production to improve clarification and filtration and to increase color extraction.

The present invention relates to a detergent composition comprising a ferulic acid esterase or an enzyme preparation of the invention and optionally one or more surfactants. Preferably a detergent composition contains an enzyme preparation of the invention comprising at least one FAE polypeptide and other enzymes selected from the group of protease, amylase, cellulase, lipase, xylanase, mannanase, cutinase, pectinase or oxidase with or without a mediator as well as suitable additives selected from the group of stabilizers, buffers, surfactants, bleaching agents, mediators, anti-corrosion agents, builders, antiredeposition agents, optical brighteners, dyes, pigments, caustics, abrasives and preservatives, etc. Cellulolytic enzymes may be used in detergent compositions, for example, for the purpose of improving fabric care properties by antipilling, antigraying, color clarification and softening, and to improve textile cleaning effect, for instance soil removal.

The enzyme preparations of the invention may contain a surfactant which can be anionic, non-ionic, cationic, amphoteric or a mixture of these types, especially when used as a detergent composition, Useful detergent compositions are described e.g. in WO 94/07998, U.S. Pat. No. 5,443,750 and U.S. Pat. No. 3,664,961.

The present invention also relates to an animal feed comprising ferulic acid esterases or enzyme preparations of the present invention. In addition the animal feed contains cereals such as barley, wheat, rye, oats, or maize, without limiting to them. Starch, proteins and lipids can be easily degraded by the digestive system of monogastric animals such as poultry and pigs, whereas the major part of non-starch polysaccharides (NSP) including mixed-linked β-glucans of e.g. barley and oats remain intact due to the lack of such enzyme activities within the animal. Furthermore, the digestibility of other components, particularly animal-based fats, is reduced in the presence of NSP. The animal feed of the invention and the enzyme preparations used in animal feed manufacturing improve utilization of the plant nutrients by the animal thus improving animal performance, which can be seen as improved weight gain and feed conversion ratio.

The invention is described by the following non-limiting examples. It will be obvious to a person skilled in the art that, as the technology advances, the inventive concept can be implemented in various ways. The invention and its embodiments are not limited to the examples described but may vary within the scope of the claims.

EXAMPLE 1

Purification of FAE Protein from *Chaetomium thermophilum* ALKO4265

Fungal strain *Chaetomium thermophilum* ALKO4265 (CBS 132416) and *Melanocarpus albomyces* ALKO4237 (CBS 132099) were grown, maintained and sporulated on Potato Dextrose (PD) agar (Difco). The PD slants of the ALKO4265 strain was inoculated into a complex culture medium which contained: 18 g/l Solka-Floc® cellulose (International Fiber Europe N.V., Belgium), 18 g/l distiller's spent grain, 9 g/l Locust bean gum, 9 g/l oats spelt xylan, 4.5 g/l soybean meal, 3 g/l wheat bran, 2 g/l $CaCO_3$, 4.5 g/l $(NH_4)HPO_4$, 1.5 g/l $KH_2PO_4$, 1.5 g/l $MgSO_4 \times H_2O$, 0.9 g/l $KNO_3$, 0.5 g/l NaCl and trace elements $MnSO_4$, $ZnSO_4$, $CoCl_2$ and $FeSO_4$. The pH of the medium was adjusted before sterilization with KOH to 6.5-7.5 and the medium was autoclaved for 15 minutes at 121° C. The microbes were cultivated on a shaker (250 rpm) at 42° C. for 7 days. Cells and solids were removed from the spent culture medium by centrifugation. The spent culture supernatants were analyzed on sodium dodecyl sulfate polyacrylamide gel electrophoresis (SDS-PAGE).

Production of FAE activity was tested in agar plate assay using ethyl cinnamate (Sigma-Aldrich, St. Louis, Mo., USA) as a substrate and Bromocresol green (Merck, Darmstadt, Germany) as a pH indicator (modified from both Donaghy and McKay, 1994 and Donaghy, Kelly and McKay, 1998). Plates were prepared autoclaving a solution with 2% agar and 5-10 mM Tris-HCl pH 6.8 for 15 minutes at 121° C., and tempered to 80° C., after which 1% Ethyl cinnamate substrate and 0.008% bromocresol green was added. The mixture was tempered to 54° C. and stirred thoroughly before it was poured to the petri dishes. Ferulic acid activity was observed as color change on the agar plate after incubating a sample droplet for 3-16 h at 30° C.

Culture supernatant of *Chaetomium thermophilum* ALKO4265 was filtered through a 0.44 μm filter (MILLEX HV Millipore, MA, USA) and concentrated 10× using Macrosep 10K centrifugal device (PALL Life Sciences, NY, USA). Five ml of concentrated sample was fractionated using Superdex 26/60 75 pg gel-filtration column (GE Healtcare Bio-Sciences, AB Sweden). The column was equilibrated with 5 mM Tris, 150 mM NaCl pH 7.5. Fractions were analysed using FAE activity plate assay and SDS PAGE analysis. Fractions shown positive staining on a plate assay were pooled. The buffer of pooled sample was changed using HiPrep 26/10 Desalting column (GE Healtcare Bio-Sciences, AB Sweden) equilibrated with 20 mM Tris pH 7.5. Sample was further fractionated using Q Sepharose HP 1 ml column (GE Healtcare Bio-Sciences, AB Sweden). Column was equilibrated with 20 mM Tris pH 7.5. FAE activity was found from flow through fraction. On SDS PAGE there was two main bands ~27 kDa and ~55 kDa in the flow through fraction. Both bands were identified by amino acid sequencing (Example 2).

EXAMPLE 2

Amino Acid Sequencing of the Purified Proteins from Chaetomium thermophilum ALKO4265

For determination of internal sequences, the Coomassie Brilliant Blue stained band was cut out of the polyacrylamide gel and "in-gel" digested essentially as described by Shevchenko et al. (1996). Proteins were reduced with dithiothreitol and alkylated with iodoacetamide before digestion with trypsin (Sequencing Grade Modified Trypsin, V5111, Promega, WI, USA) and mass determination.

Electrospray ionization quadrupole time-of-flight tandem mass spectra for de novo sequencing were generated using a Q-TOF instrument (Micromass, Manchester, UK) connected to an Ultimate nano liquid chromatograph (LC-Packings, The Netherlands) essentially as described previously (Poutanen et al., 2001) but using a 150 μm×1.0 mm trapping column (3 μm, 120 Å, #222403, SGE Ltd, UK) for peptide preconcentration.

For N-terminal sequence analysis SDS-PAGE separated proteins were transferred by electroblotting into a polyvinylidine difluoride membrane (ProBlott; Perkin Elmer Applied Biosystems Division, CA, USA) After being stained with Coomassie brilliant blue, the protein bands of interest were removed and subjected to N-terminal sequence analysis by Edman degradation on a Procise 494A protein sequencer (Perkin Elmer Applied Biosystems Division, CA, USA).

The peptide sequences determined from the purified proteins were analyzed. Internal peptides from a 55 kDa purified protein from Chaetomium thermophilum ALKO4265 showed similarity to a published feruloyl esterase from Neurospora grassa (accession number XP_963215). N-terminal peptide from a 27 kDa purified protein from Chaetomium thermophilum ALKO4265 showed similarity to a published feruloyl esterase from Neurospora grassa with accession number XP_963215. The protein of interest (from Chaetomium thermophilum ALKO4265) was thus named Ct_FAE. The internal and N-terminal peptide sequences obtained from protein Ct_FAE (SEQ ID NOs: 1-4) are shown in Table 1.

TABLE 1

Internal peptide sequences determined from the purified proteins Ct_FAE from Chaetomium thermophilum

| Protein Ct_FAE | Peptide | Sequence | SEQ ID NO: | Comment |
|---|---|---|---|---|
| Internal | 1199,656 | TPEEWGNLVR | 1 | de novo; L can be L or I |
| Internal | 1414,697 | QWSNVLGLELTR | 2 | de novo; L can be L or I |
| Internal | 1906,045 | GETQHLYGDGTK | 3 | de novo; L can be L or I |
| N-terminal | #4276 | ASLQQVSNFGSN | 4 | N-terminus |

EXAMPLE 3

Cloning of the Fae Genes from Chaetomium thermophilum ALKO4265 and Melanocarpus albomyces ALKO4237

Standard molecular biology methods were used in the isolation and enzyme treatments of DNA (e.g. isolation of plasmid DNA, digestion of DNA to produce DNA fragments), in E. coli transformations, sequencing etc. The basic methods used were either as described by the enzyme, reagent or kit manufacturer or as described in the standard molecular biology handbooks, e.g. Sambrook and Russell (2001). Isolation of genomic DNA was performed as described in detail by Raeder and Broda (1985).

Degenerate oligonucleotides were planned basing on the amino acid sequences of the peptides obtained from the purified Ct_FAE protein (Table 1). The degenerate oligos were used to synthesize probes for the genes encoding the proteins from Chaetomium thermophilum ALKO4265.

In addition, several other thermophilic strains were analysed by using degenerate primers from Chaetomium thermophilum, and surprisingly probe from Melanocarpus albomyces ALKO4237 was obtained by heterologous cloning. Sequences of the degenerate oligos used as primers are shown in Table 2 (SEQ ID NOs: 5-6).

TABLE 2

The oligonucleotides used as PCR primers to amplify probes for fae genes from *Chaetomium thermophilum* ALKO4265 and *Melanocarpus albomyces* ALKO4237

| Template, genomic DNA from | Peptide[a] | Oligo-nucleotide | Length (bp) | Sequence[b] | SEQ ID NO: |
|---|---|---|---|---|---|
| ALKO4265 | #4276 | FAEF1 | 20 | CARCARGTNTCNAAYTTGG (s) | 5 |
|  | 1414,697 | FAER2 | 20 | CCNARNACRTTNGACCAYTG (as) | 6 |

[a]The peptide sequences are included in Table 1.
[b]N = A or G or T or C, Y = T or C, R = A or G,; "s" in the parenthesis = sense strand, "as" in the parenthesis = antisense strand.

Primer combination of FAEF1 and FAER2 (SEQ ID NOs: 5 and 6) produced a 898 bp PCR product with *Chaetomium thermophilum* ALKO4265 genomic DNA as template in PCR conditions containing 1× Phusion HF buffer, 0.2 mM dNTPs, 1 µM of primers FAEF1 and FAER2 (Table 2), 4 units of Phusion DNA polymerase (Finnzymes, Finland), 3% DMSO, and 1.5 µg of the ALKO4265 genomic DNA per 200 µl reaction volume. The conditions for the PCR reactions were the following: 30 sec initial denaturation at 98° C., followed by 25 cycles of 10 sec at 98° C., 30 sec annealing at 52.5° C. (±7.5° C. gradient), 30 sec extension at 72° C. and a final extension at 72° C. for 7 min. The PCR product was isolated and purified from the PCR reaction mixture and cloned to pCR® 4Blunt-TOPO®-vector according to the manufacturer's instructions (Invitrogen, USA). The insert was characterized by sequencing.

Primer combination of FAEF1 and FAER2 (SEQ ID NOs: 5 and 6) produced a 855 bp PCR product with *Melanocarpus albomyces* ALKO4237 genomic DNA as template. PCR conditions and methods for product isolation, purification, cloning to pCR® 4-TOPO-TA®-vector and sequencing were identical to those with *Chaetomium thermophilum* ALKO4265 above.

The deduced amino acid sequences from both of these PCR fragments had similarity to the published FAE sequences (BLAST program, version 2.2.9 at NCBI, National Center for Biotechnology Information). Thus the unknown genes were named Ct_fae and Ma_fae.

The obtained PCR fragments chosen to be used as probes for cloning of the full-length genes from the *Chaetomium thermophilum* ALKO4265 and *Melanocarpus albomyces* ALKO4237 strains are presented in Table 3.

TABLE 3

Probes chosen for cloning of the full-length fae genes from strains *Chaetomium thermophilum* ALKO4265 and *Melanocarpus albomyces* ALKO4237. The genomic template DNA, primers used in the PCR reactions, size of the PCR fragments obtained, the name of the plasmid containing the probe fragment and SEQ ID NOs of the probe sequences are shown.

| Genomic DNA used as a template in PCR reaction | Primers | PCR fragment obtained (bp) | Insert in plasmid | SEQ ID NO: |
|---|---|---|---|---|
| ALKO4265 | FAEF1, FAER2 | 898 bp | pALK3204 | 7 |
| ALKO4237 | FAEF1, FAER2 | 855 bp | pALK3206 | 8 |

The pCR® 4-TOPO® plasmid containing the PCR amplified probe for cloning the full-length gene encoding Ct_FAE was named pALK3204 and the *E. coli* strain including this plasmid, RF9344, was deposited to the DSM collection under the accession number DSM26068. The pCR® 4-TOPO® plasmid containing the PCR amplified probe for gene Ma_fae was named pALK3206 and the *E. coli* strain including this plasmid, RF9346, was deposited to the DSM collection under the accession number DSM26069.

*Chaetomium thermophilum* ALKO4265 and *Melanocarpus albomyces* ALKO4237 genomic DNAs were digested with several restriction enzymes for Southern blot analysis. The probes for the hybridizations were the PCR fragments having SEQ ID NO: 7 and SEQ ID NO: 8 cut with EcoRI digestion or PCR amplified from the plasmids pALK3204 and pALK3206, respectively. The above probes were labeled by using digoxigenin according to supplier's instructions (Roche, Germany). Hybridizations were performed over night at 68° C. After hybridization the filters were washed 2×5 min at RT using 2×SSC–0.1% SDS followed by 2×15 min at 68° C. using 0.1×SSC–0.1% SDS.

From the genomic DNA of *Chaetomium thermophilum* ALKO4265, an approximately 4.8 kb HindIII-digested fragment was obtained. From the genomic DNA of *Melanocarpus albomyces* ALKO4237, an approximately 4.8 kb SacI-digested fragment was obtained with the dioxigenin-labeled probe fragment from plasmid pALK3206. The hybridized genomic DNA fragments were isolated from the pool of the digested genomic fragments based on their size. The genomic fragments were isolated from agarose gel and were cloned to pBluescript II KS+ (Stratagene, CA, USA) vectors cleaved with HindIII or SacI. Ligation mixtures were transformed to *Escherichia coli* XL10-Gold cells (Stratagene, CA, USA) and plated on LB (Luria-Bertani) plates containing 50-100 µg/ml ampicillin. The *E. coli* colonies were screened for positive clones using colonial hybridization with the pALK3204 and pALK3206 inserts as probes in the hybridization conditions correspondingly to that described above for Southern blot analyses (the only difference was 65° C. hybridization temperature). Several positive clones were collected from the plates. They were shown by restriction digestion to contain inserts of expected sizes and the inserts were further screened using Southern hybridization with the pALK3204 and pALK3206 inserts as a probe. Southern blot was performed on inserts of the collected clones with hybridization performed at 65° C. and washed 2×5 min at RT using 2×SSC–0.1% SDS followed by 2×15 min at 65° C. using 0.1×SSC–0.1% SDS.

The full-length gene encoding the *Chaetomium thermophilum* ALKO4265 protein Ct_FAE was sequenced from the 4.8 kb HindIII insert and the plasmid containing this insert was named pALK3216. The *E. coli* strain RF9727 including the plasmid pALK3216 was deposited to the DSM collection under the accession number DSM26071. The gene encoding the *Chaetomium thermophilum* ALKO4265 protein Ct_FAE is named as Ct_fae (SEQ ID NO:9). Correspondingly, the full-length fae gene encoding the Ma_FAE was sequenced from the 4.8 kb SacI insert and the plasmid containing this insert was named pALK3214. The *E. coli* strain RF9726 including the plasmid pALK3214 was deposited to the DSM collection under the accession number DSM26070. The gene encoding the *Melanocarpus albomyces* ALKO4237 protein Ma_FAE is named as Ma_fae (SEQ ID NO:10). The relevant information on the gene sequences (SEQ ID NOs: 9 and 10) is summarized in Table 4.

TABLE 4

The summary on the fae genes isolated from *Chaetomium thermophilum* ALKO4265 and *Melanocarpus albomyces* ALKO4237. The gene lengths with and without introns and the SEQ ID NOs of the genes are shown.

| Gene | Length with introns (bp)[a] | Coding region (bp)[b] | No of putative introns | Lengths of putative introns (bp) | SEQ ID NO: |
|---|---|---|---|---|---|
| Ct_fae | 1115 | 867 | 2 | 65, 180 | 9 |
| Ma_fae | 1080 | 813 | 3 | 80, 120, 64 | 10 |

[a]The STOP codon is included.

[b]The STOP codon is not included.

The deduced amino acid sequence of the gene Ct_fae included the sequences of the Ct_FAE peptides 1199,656 (SEQ ID NO: 1), 1414,697 (SEQ ID NO: 2), 1906,045 (SEQ ID NO: 3), and #4276 (SEQ ID NO: 4) (Table 1). This confirms that the gene Ct_fae obtained from the cloning is the gene encoding the purified Ct_FAE protein. The deduced amino acid sequence of gene Ma_fae included the sequences of the Ma_FAE peptide #4276 (SEQ ID NO:4) and the protein deduced from the gene sequence Ma_fae is named Ma_FAE. The relevant information on the deduced protein sequences (SEQ ID NOs: 11 and 12) is summarized in Table 5.

TABLE 5

The summary of the amino acid sequences deduced from the fae gene sequences from *Chaetomium thermophilum* ALKO4265 and *Melanocarpus albomyces* ALKO4237.

| Gene | Protein | No of aas | Length of ss aas[a] | Predicted MW (kDa)[b] | Predicted pI[b] | SEQ ID NO: |
|---|---|---|---|---|---|---|
| Ct_fae | Ct_FAE | 289 | 18 | 29.6 | 6.84 | 11 |
| Ma_fae | Ma_FAE | 271 | 18 | 27.5 | 6.12 | 12 |

[a]The prediction on the signal sequence was made using the program SignalP V3.0 (Nielsen et al., 1997; Nielsen and Krogh, 1998; Bendtsen et al., 2004).

[b]The predicted signal sequence was not included. The prediction was made using the Clone Manager 9 programme.

The comparison of the deduced FAE sequences from *Chaetomium thermophilum* ALKO4265 and *Melanocarpus albomyces* ALKO4237 to the sequences found from databases are shown in Table 6.

TABLE 6

The highest identity sequences to the deduced FAE amino acid sequences from *Chaetomium thermophilum* ALKO4265 and *Melanocarpus albomyces* ALKO4237. The full-length amino acid sequences including the signal sequences were aligned. The database search was performed at http://www.ebi.ac.uk/Tools/sss/fasta/ using FASTA (EMBL-EBI, FASTA - Protein Similarity Search, UniProt Knowledgebase and NRPL 1, BLOSUM62 Gap open -7, Gap extend -1), and EMBOSS Needle (EMBL-EBI, EMBOSS-Needle - Pairwise Sequence Alignment, BLOSUM62, Gap open 10, gap extend 0.5) at http://www.ebi.ac.uk/Tools/psa/emboss needle/ was used for determining the degree of identity.

| Organism and accession number | Identity (%) |
|---|---|
| Ct_FAE | 100 |
| US20090151026 | 75 |
| Ma_FAE | 100 |
| US20090151026 | 72 |

EXAMPLE 4

Production of Recombinant FAE Proteins in *Trichoderma reesei*

Expression plasmids were constructed for production of recombinant FAE proteins from *Chaetomium thermophilum* ALKO4265 and *Melanocarpus albomyces* ALKO4237 in *Trichoderma reesei*. The recombinant fae genes, including their own signal sequences, were exactly fused to the *T. reesei* cbh1/cel7A promoter by PCR. A BamHI site was created after the stop codon by PCR to fuse the gene at the 3"-end to the *T. reesei* cbh1/cel7A terminator. This leaves no original terminator in the constructs prior to the cbh1 terminator sequence. The *A. nidulans* amdS marker gene was used for selection of the transformants as described in Paloheimo et al. (2003). The linear expression cassettes (FIG. 1) were isolated from the vector backbones after either NotI digestion (Ct_fae) or EcoRI digestion (Ma_fae). The expression cassettes of Ct_fae (6468 bp) and Ma Jae (6424 bp) were transformed into *T. reesei* protoplasts. The host strain used does not produce any of the four major *T. reesei* cellulases (CBHI, CBHII, EGI, EGII). The transformations were performed as in Penttilä et al. (1987) with the modifications described in Karhunen et al. (1993), selecting acetamide as a sole nitrogen source (amdS marker gene). The transformants were purified on selection plates through single conidia prior to sporulating them on PD.

The FAE protein production of the transformants was analysed from the culture supernatants of the shake flask cultivations. The transformants were inoculated from the PD slants to shake flasks containing 50 ml of complex lactose-based cellulase inducing medium (Joutsjoki et al., 1993) buffered with 5% $KH_2PO_4$. The FAE protein production was analyzed after cultivation for 7 days at 30° C., 250 rpm. Heterologous production of recombinant proteins was analyzed by SDS-PAGE with subsequent Coomassie staining. The genotypes of the chosen transformants were confirmed by Southern blot analyses in which genomic digests were included and the respective expression cassette was used as a probe.

The best-producing transformants were chosen to be cultivated in laboratory scale bioreactors at 28° C. in the cellulase inducing complex medium for 3-4 days with pH control 4.5±0.2 or 5.5±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany)

EXAMPLE 5

Hydrolysis of Bagasse Substrate with Enzyme Preparations Comprising Recombinant FAE Proteins Bagasse was suspended in 0.05 M sodium citrate buffer, pH 4.8. The final weight of the hydrolysis mixture was 1 g of which the total solids concentration was 12% (w/w). The substrate was hydrolysed using different enzyme mixtures at a dosage of 2 mg of protein per gram of total solids in 2 ml reaction tubes. The protein contents of the enzyme components were determined using the Pierce BCA assay kit, Product number 23227 (Thermo Scientific, MA, USA) with Bovine Serum Albumin, Product number 23209 (Thermo Scientific, MA, USA) as standard. The reaction tubes were agitated in a linear-shaking waterbath 1086 from GFL adjusted in different temperatures. For each sample point, a sample of 0.5 ml was taken from duplicate reaction tubes and centrifuged. The supernatant was boiled for 20 minutes to terminate the enzymatic hydrolysis, and analysed for reaction products from the hydrolysis.

A basis mixture of different thermostable lignocellulolytic enzymes was prepared using the following components:

CBHI/Cel7A preparation containing recombinant *Acremonium thermophilum* ALKO4245 CBHI/Cel7A (WO2007071818), CBHII/Cel6A preparation containing recombinant *Acremonium thermophilum* ALKO4245 CBHII/Cel6A (WO2011080317), EGII/Cel5A preparation containing recombinant *Thermoascus aurantiacus* ALKO4242

EGII/Cel5A (WO2007071818) with genetically attached CBM of *Trichoderma reesei* EGII/Cel5A (WO2007071818), Mesophilic EGI/Cel7B preparation containing recombinant *Trichoderma reesei* EGI/Cel7B, β-glucosidase preparation containing *Acremonium thermophilum* ALKO4245 β-glucosidase/Cel3A (WO2007071818), Xylanase preparation containing *Thermoascus aurantiacus* ALKO4242 Xyn10A xylanase (WO2007071818).

All cellulases were heterologously produced as monocomponents in *Trichoderma reesei* host strain having cellulase-free background (the genes encoding the four major cellulases CBHI/Cel7A, CBHII/Cel6A, EGI/Cel7B and EGII/Cel5A were deleted). Crude culture supernatants were used in the mixture. The enzyme components were combined as follows to prepare a basis mixture: cellobiohydrolase CBHI/Cel7A preparation 60%, cellobiohydrolase CBHII/Cel6A preparation 15%, endoglucanase EGII/Cel5A preparation 10%, endoglucanase EGI/Cel7B preparation 8%, xylanase Xyn10A preparation 3% and β-glucosidase βG/Cel3A preparation 4%. This enzyme mixture was designated as MIXTURE 1.

For testing FAE molecule performance in the hydrolysis three separate mixture combinations were prepared containing 80%, 90% or 95% of MIXTURE 1 and 20%, 10% or 5% of following FAE components:

*Chaetomium thermophilum* FAE enzyme preparation (Ct_FAE) and

*Melanocarpus albomyces* FAE enzyme preparation (Ma_FAE).

Figure 2:
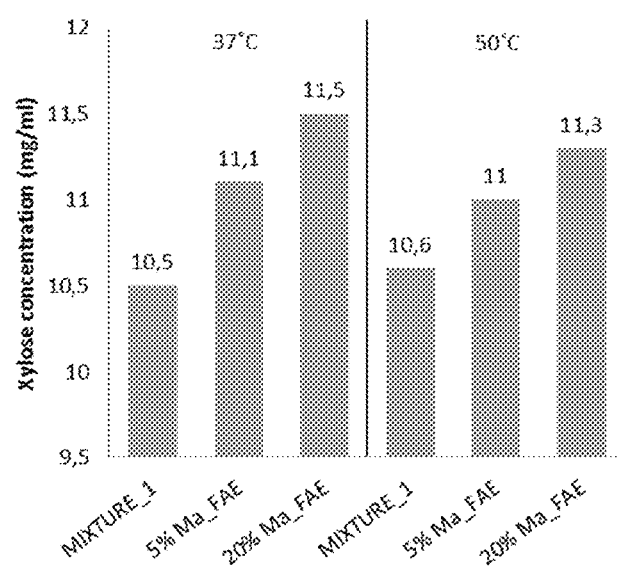
FIG. 2 shows results from hydrolysis of bagasse substrate performed with enzyme mixtures comprising the *Melanocarpus albomyces* FAE (Ma_FAE) enzyme of the invention. The bagasse substrate with 12% dry matter was hydrolyzed using different enzyme mixtures at a dosage of 2 mg of protein per gram of total solids at 37° C. and 50° C. Detailed compositions of the control enzyme mixture and composition comprising the tested FAE protein are described in Example 5. Samples from triplicate tubes were taken after 48 hours hydrolysis time and quantified by HPLC, in which the concentration of xylose was determined.

For all mixtures the hydrolysis was performed at 37° C. and 50° C. Samples were taken from the hydrolysis after 48 h, quantified by HPLC and the concentration of xylose was determined. Results of the Ma_FAE hydrolysis is shown in FIG. 2.

The results show better performance of the Ma_FAE at tested temperatures (37° C. and 50° C.) in comparison to the control MIXTURE 1. At 50° C. the Ma_FAE performed up to 7% better (with 20% Ma_FAE) than the control mix MIXTURE 1. At 37° C. the Ma_FAE performed up to 10% better (with 20% Ma_FAE) than the control mix MIXTURE 1.

EXAMPLE 6

Removal of Fibrous Residues from Automatic Dishwasher Filters with Enzyme Preparations Comprising Recombinant FAE Enzymes Hydrolysis of fibrous residues building up in automatic dishwashers was measured with ground fibers from apples, oranges and wheat suspended in dilute citrate buffer, pH 4.0 containing ca. 0.5% propylene glycol in 500 ml shake flasks. Equal amount of each fiber was added and the final total solids concentration was 4 g per liter. Enzymes were added at a dosage of 25 mg of protein per gram of total solids. The amount of protein from the enzyme preparations was determined by Bio-Rad protein assay (Bio-Rad Laboratories, Hercules, Calif., USA) using bovine gammaglobulin (Bio-Rad Laboratories, Hercules, Calif., USA) as standard. The hydrolysis experiments were performed at 50° C. and 60° C. The flasks containing fibers and enzymes in dilute citrate buffer were heated to 50° C./60° C. in 230 rpm shaking. After 60 min incubation time at 50° C./60° C., the solution was filtered through a 200 μm mesh and the fibers left on the sieve dried for at least 20 h at 50° C. The dried fibers were weighed to measure the weight loss of the fibers. Weight loss was calculated as percentage of the weight of a blank. The blank containing fiber alone in the buffer (no enzymes) was prepared identically to the other samples.

Basic *Trichoderma reesei* cellulase mixture (Roal Oy, a classical *T. reesei* enzyme product) was used in the comparison. Enzyme mixtures contained basic *T. reesei* cellulase mixture alone (control) or a mixture containing 72% (18 mg) of *T. reesei* cellulase mixture and 28% (7 mg) of Ct_FAE or Ma_FAE for testing FAE performance in the hydrolysis. The FAE enzymes were heterologously produced as monocomponents in *Trichoderma reesei* host strain having cellulase-free background (the genes encoding the four major cellulases CBHI, CBHII, EGI and EGII were deleted). Crude culture supernatants were used in the enzyme mixtures.

Figure 3:
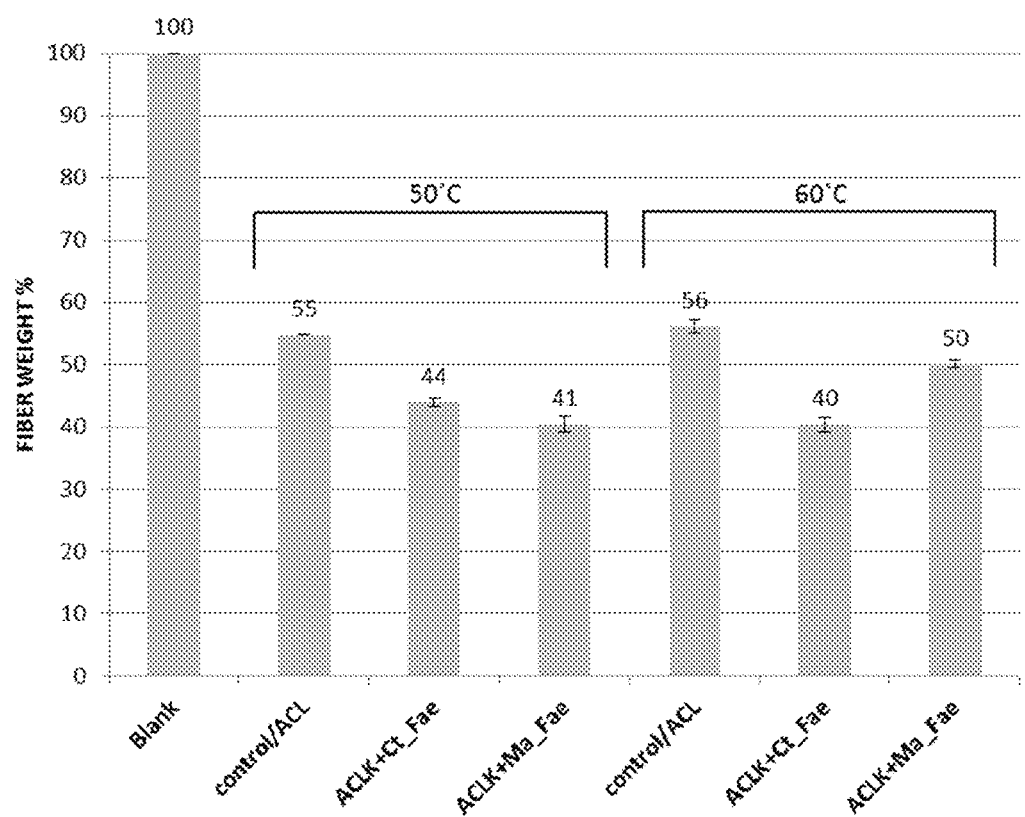
FIG. 3 shows results from hydrolysis of ground apple/orange/wheat fibre mixture performed with enzyme mixtures comprising the FAE proteins of the invention. Percentage of fiber weight after 60 min hydrolysis at 50° C. or 60° C. is presented for the control and mixtures containing FAE proteins Ma_FAE or Ct_FAE. Standard deviations are included in the graph.

The average results from triplicate samples of the control and samples containing the FAE proteins are shown in FIG. 3. When the basic *T. reesei* cellulase mixture was partly replaced with *Chaetomium thermophilum* Ct_FAE, the weight of the fiber residues left in the sieve was found to decrease 20% in 50° C. and 29% in 60° C. Respectively, when the basic *T. reesei* cellulase mixture was partly replaced with *Melanocarpus albomyces* Ma_FAE enzymes, the weight of the fiber residues left in the sieve was found to decrease 25% in 50° C. and 11% in 60° C. The results show, thus, better performance when the *T. reesei* cellulase mixture is supplemented with FAE protein Ct_FAE or Ma_FAE.

EXAMPLE 7

The Digestibility of Nutrients and Growth Performance after Addition of an Enzyme Preparation Containing Recombinant FAE Proteins to Broiler Feed Pelleted animal feed comprising either wheat and soy or corn and soy is treated by spraying enzyme solution onto the pellets. The enzyme solution sprayed onto the pellets contains different combinations of enzymes including Ct_FAE or Ma_FAE alone or in combination with xylanase. The enzymes are dosed at levels of between 1 and 200 g/t. The performance of FAE enzymes is compared to the effect of xylanase alone.

Each treatment has six replicates and observational unit is pen of 20 broilers. In each case the diet is analyzed for moisture, crude protein, crude fibre, oil, ash, calcium, phosphorous, $TiO_2$ marker, and neutral detergent fibre (NDF).

Initial weight of the broilers is between 30 g and 50 g. The trial lasts between 35 and 55 days. During the trial body weight gain, feed intake, and feed-conversion ratio (FCR) are measured at the beginning of the trial and at between 15 and 25 days and again after 35 to 55 days. FCR is calculated as the total feed consumed divided by the weight gain during the same period.

Health status of the animals is checked daily by visual inspection. Feed samples and composite faecal samples from each pen are analyzed for dry matter, $TiO_2$ markers, nitrogen, and Gross Energy (GE). The determination of the effect of the recombinant FAE proteins is based on FCR, efficiency of feed utilization, apparent total tract nitrogen, dry matter and energy digestibilities. GE is determined using an adiabatic bomb calorimeter. Apparent total tract nitrogen ($ATTD_N$), dry matter ($ATTD_{DM}$) and energy digestibilities ($ATTD_E$) are determined as follows: Titanium dioxide is assayed in the feed and excreta material using the method described by Short et al (1996). The following calculation is then used where X is the component of interest (ie, nitrogen, DM, energy):

$$ATTD_X = 100\% - [((TT_S \times X_F)/(X_D \times TT_F)) \times 100\%];$$

where $ATTD_X$=AID of component in the assay ingredient (%), $TT_D$=Ti02 concentration in the assay diet (g/kg DM), $X_F$=nutrient concentration in excreta (g/kg DM), $X_D$=nutrient concentration in the assay diet (g/kg DM) and TTF=marker concentration in excreta (g/kg DM).

REFERENCES

Bendtsen J D, Nielsen H, von Heijne G, and Brunak S. (2004) Improved prediction of signal peptides: SignalP 3.0. J. Mol. Biol. 340:783-795.

Coen D M. (2001) The polymerase chain reaction. In: Ausubel F M., Brent R., Kingston R E., More D D., Seidman J G., Smith K. and Struhl K. (eds.) Current protocols in molecular biology. John Wiley & Sons. Inc., Hoboken, USA.

Donaghy J A, and McKay A M. (1994) Novel screening assay for the detection of phenolic acid esterases. World J. Microb. Biot. 10: 41-44.

Donaghy J A, Kelly P F, and McKay A M. (1998) Detection of ferulic acid esterase production by *Bacillus* spp. and lactobacilli. Appl Microbiol Biotechnol 50: 257-260.

Gellissen G. (ed.) (2005) Production of recombinant proteins. Novel microbial and eukaryotic expression systems. Wiley-VCH Verlag Gmbh&Co. Weinheim, Germany Joutsjoki V V, Torkkeli T K, and Nevalainen K M H. (1993) Transformation of *Trichoderma reesei* with the *Hormoconis resinae* glucoamylase P (gamP) gene: production of a heterologous glucoamylase by *Trichoderma reesei*. Curr. Genet. 24: 223-228.

Karhunen T, Mantyla M, Nevalainen K M H, and Suominen P L. (1993) High frequency one-step gene replacement in *Trichoderma reesei*. I. Endoglucanase I overproduction. Mol. Gen. Genet. 241: 515-522.

Kühnel, S., Pouvreau, L., Appeldoorn, M. M., Hinz, S. W. A, Schols, H. A. and Gruppen, H. (2012) "The Ferulic Acid Esterases of *Chrysosporium Lucknowense* C1: Purification, Characterization and Their Potential Application in Biorefinery." Enzyme and Microbial Technology 5; 50(1): 77-85.

Needleman S. and Wunsch C. (1970) A general method applicable to the search for similarities in the amino acid sequence of two proteins. Journal of Molecular Biology 48, 443-453.

Nielsen H, Engelbrecht J, Brunak S, and von Heijne G. (1997) Identification of prokaryotic and eukaryotic signal peptides and prediction of their cleavage sites. Protein. Eng. 10:1-6.

Nielsen H, and Krogh A. (1998) Prediction of signal peptides and signal anchors by a hidden Markov model. In: Proceedings of the Sixth International Conference on Intelligent Systems for Molecular Biology (ISMB 6), AAAI Press, Menlo Park, Calif., p. 122-130.

Paloheimo M, Mantyla A, Kallio J, and Suominen P. (2003) High-yield production of a bacterial xylanase in the filamentous fungus *Trichoderma reesei* requires a carrier polypeptide with an intact domain structure. Appl. Env. Microbiol. 69: 7073-7082.

Penttilä M, Nevalainen H, Rättö M, Salminen E, and Knowles J. (1987) A versatile transformation system for the cellulolytic filamentous fungus *Trichoderma reesei*. Gene 61: 155-164.

Poutanen M, Salusjärvi L, Ruohonen L, Penttilä M, and Kalkkinen N. (2001) Use of matrix-assisted laser desorption/ionization time-of-flight mass mapping and nanospray liquidchromatography/electrospray ionization tandem mass spectrometry sequence tag analysis for high sensitivity identification of yeast proteins separated by two-dimensional gel electrophoresis. Rapid Commun Mass Spectrom. 15: 1685-1692.

Raeder U, and Broda P. (1985) Rapid preparation of DNA from filamentous fungi. Lett. Appl. Microbiol. 1: 17-20.

Sambrook J, and Russell D W. (2001) Molecular cloning, a laboratory manual. Cold Spring Harbor Laboratory, New York, US.

Shevchenko A, Wilm M, Vorm O, and Mann M. (1996) Mass spectrometric sequencing of proteins from silver-stained polyacrylamide gels. Anal. Chem. 68: 850-858.

Short, F. J., Gorton, P., Wiseman, J., Boorman, K. N., 1996. Determination of titanium dioxide added as an inert marker in chicken digestibility studies. Anim. Feed. Sci. Technol. 59, 215-221.

Visser H, Joosten V, Punt P J, Gusakov A V, Olson P T, Joosten R, Bartels J, Visser J, Sinitsyn A P, Emalfarb M A, Verdoes J C, and Wery J. (2011) Development of a mature fungal technology and production platform for industrial enzymes based on the *Myceliphthora thermophile* isolate, previously known as *Chrysosporium lucknowense* C1. Industrial Biotechnology. 7: 214-223.

DEPOSITIONS

| Deposited strain | Culture collection | Deposition date | Accession number |
|---|---|---|---|
| *Melanocarpus albomyces* ALKO4237 | 1) | 2 Mar. 2012 | CBS132099 |
| *Chaetomium thermophilum* ALKO4265 | 1) | 14 Apr. 2012 | CBS132416 |
| The *E. coli* strain RF9344 including the plasmid pALK3204 | 2) | 13 Jun. 2012 | DSM26068 |
| *E. coli* strain RF9346 including the plasmid pALK3206 | 2) | 13 Jun. 2012 | DSM26069 |
| *E. coli* strain RF9726 including the plasmid pALK3214 | 2) | 13 Jun. 2012 | DSM26070 |
| *E. coli* strain RF9727 including the plasmid pALK3216 | 2) | 13 Jun. 2012 | DSM26071 |

1) Centraalbureau Voor Schimmelcultures at Upsalalaan 8, 3508 AD, Utrecht, the Netherlands
2) Deutsche Sammlung von Mikroorganismen and Zellkulturen GmbH (DSMZ), Inhoffenstrasse 7B, D-38124 Braunschweig, Germany

---

The invention claimed is:

1. A detergent composition comprising an enzyme preparation comprising a recombinant polypeptide having ferulic acid esterase activity and comprising an amino acid sequence having at least 90% sequence identity to an amino acid sequence of SEQ ID NO: 11 or SEQ ID NO: 12 in a spent culture medium, wherein the enzyme preparation further comprising additives.

2. The detergent composition according to claim 1, wherein the composition is a dishwashing machine cleaning composition.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Chaetomium thermophilum
<220> FEATURE:
<221> NAME/KEY: SOURCE
<222> LOCATION: 1..10
<223> OTHER INFORMATION: /mol_type="protein"
      /organism="Chaetomium thermophilum"

<400> SEQUENCE: 1

Thr Pro Glu Glu Trp Gly Asn Leu Val Arg
1               5                   10

<210> SEQ ID NO 2
<211> LENGTH: 12
<212> TYPE: PRT
<213> ORGANISM: Chaetomium thermophilum
<220> FEATURE:
<221> NAME/KEY: SOURCE
<222> LOCATION: 1..12
<223> OTHER INFORMATION: /mol_type="protein"
      /organism="Chaetomium thermophilum"

<400> SEQUENCE: 2

Gln Trp Ser Asn Val Leu Gly Leu Glu Leu Thr Arg
1               5                   10

<210> SEQ ID NO 3
<211> LENGTH: 12
<212> TYPE: PRT
<213> ORGANISM: Chaetomium thermophilum
<220> FEATURE:
<221> NAME/KEY: SOURCE
<222> LOCATION: 1..12
<223> OTHER INFORMATION: /mol_type="protein"
      /organism="Chaetomium thermophilum"

<400> SEQUENCE: 3

Gly Glu Thr Gln His Leu Tyr Gly Asp Gly Thr Lys
1               5                   10

<210> SEQ ID NO 4
<211> LENGTH: 12
<212> TYPE: PRT
<213> ORGANISM: Chaetomium thermophilum
<220> FEATURE:
<221> NAME/KEY: SOURCE
<222> LOCATION: 1..12
<223> OTHER INFORMATION: /mol_type="protein"
      /organism="Chaetomium thermophilum"
```

<210> SEQ ID NO 4

Ala Ser Leu Gln Gln Val Ser Asn Phe Gly Ser Asn
1               5                   10

<210> SEQ ID NO 5
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="primer"
      /organism="Artificial Sequence"

<400> SEQUENCE: 5
carcargtnt cnaayttgg                                            19

<210> SEQ ID NO 6
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="primer"
      /organism="Artificial Sequence"

<400> SEQUENCE: 6
ccnarnacrt tngaccaytg                                           20

<210> SEQ ID NO 7
<211> LENGTH: 898
<212> TYPE: DNA
<213> ORGANISM: Chaetomium thermophilum
<220> FEATURE:
<221> NAME/KEY: source
<222> LOCATION: 1..898
<223> OTHER INFORMATION: /mol_type="DNA"
      /organism="Chaetomium thermophilum"

<400> SEQUENCE: 7
cagcaggtgt cgaactttgg gtccaaccct acaaacatca acatgcacat ctacgtgcct    60
gacagactgg ccagcaagcc gcctatcatc gttgctgtaa gccatgagca agccacctgt   120
cgtgaaagaa gttagtctag gttaacatga acaatgttca gttgcatcct tgcggcggca   180
atgctcagca gtggttcagc ggcacgcggt tgccgcagta tgctgacagt catggcttca   240
tcctcattta cccaagtact cctcacatga gcaactgctg ggatgtgcaa aaccccgcta   300
gcttgactca tggtgccggt ggtgatgctc ttggtatcgt cagcatggta aactacgcca   360
ttaatcggta cggagccgac cgcgaccgcg tctacgccat gggcttctct tccggtggca   420
tgatgaccaa tgtgctggcg ggctcgtacc ccgatgtctt cgaggctggg gcggcttact   480
ccggtgttcc tcatgcttgc ttccttggta tgtatcgctc tcctttccat tttctgaata   540
ctcatcgagg gctcggaagc ggtccggtgt tggcctgaat atcatgagca tttgctcctt   600
caagcctcca gcgaactcta cgagcatggg gcctaccact ctggaaccat tgatcgtgaa   660
ttagctaatc atcctgctcc cttataggtg ctcccgctgc cactccgttc agccccaacc   720
aaacctgtgc tcagggtctg cagaagaccc ccgaggaatg gggcaacctt gtgcgtaatt   780
cttaccctgg ttacaatggc cgccggccgc ggatgcagat cacgcacggc ctgaacgact   840

```
ggcttgtcag gcctcagtgt gcctatgaga ctctcaagca gtggtccaac gttcaagg      898
```

<210> SEQ ID NO 8
<211> LENGTH: 855
<212> TYPE: DNA
<213> ORGANISM: Melanocarpus albomyces
<220> FEATURE:
<221> NAME/KEY: source
<222> LOCATION: 1..855
<223> OTHER INFORMATION: /mol_type="DNA"
      /organism="Melanocarpus albomyces"

<400> SEQUENCE: 8

```
cagcaggttt ctaatttcgg caacaacccg accaacatcc agatgcacat ctatgtgcct       60
gacagggtcg ccagcaaccc agcaatcatc gtggcggtga gtgctcgaag agcggcgctt      120
gctcaccccc tggaagttct ctgtgcattt ggctcacttg tgtcaccacg taccagcttc      180
atccctgcgg cggcaatgcc cagcagtggt tcggcggcac ccggctgccg tcgtacgccg      240
accagcacgg cttcatcctc atctaccccca gcactccgca catgagcaac tgctggggac      300
gtgcacaatc cggccagctt gacccatggg gcagggcgg agatgcgctt gggcatcgtc       360
agcatggtga actacgcctg aaccagtaca acggcgaccg caaccgcgtc tatgccatgg      420
gcttctcgtc ggcgggcatg atgaccaacg tcctggcggg ctcgtacccc gacgtgttcg      480
aggctggcgc ggcctatctg gcgtgccccc atgcatgctt cttgggtacg tggtgattga      540
tgttgatgct gcggcctgtg tggcggtggt cgtggcgttg tccctccggc agcgagagtc      600
tcgacgacgg cgagatgact gacgcatgtt cctcccgacg acaggtgcac ctgccgccac      660
gccgttcagc cccaaccaga cctgcgccca gggcctccag aagacggagc aggaatgggg      720
cgacctggtg cgcaactcgt atcccggcta cacgggccgg cggccgcgca tgcagatcac      780
gcacggcctg gccgacttcc tggtgcggcc gcagtgcgcg tacgaggcgc tcaagcagtg      840
gtcaaatgtc ctagg                                                       855
```

<210> SEQ ID NO 9
<211> LENGTH: 1115
<212> TYPE: DNA
<213> ORGANISM: Chaetomium thermophilum
<220> FEATURE:
<221> NAME/KEY: source
<222> LOCATION: 1..1115
<223> OTHER INFORMATION: /mol_type="DNA"
      /organism="Chaetomium thermophilum"

<400> SEQUENCE: 9

```
atgcacctcc cgtctttgct cgggctcgcc gccatggcga gcagctgcct tgctgcctcc       60
ctccagcagg tttcgaactt cgggtccaac cctacaaaca tcaacatgca catctacgtg      120
cctgacagac tggccagcaa gccgcctatc atcgttgctg taagccatga gcaagccacc      180
tgtcgtgaaa gaagttagtc taggttaaca tgaacaatgt tcagttgcat ccttgcggcg      240
gcaatgctca gcagtggttc agcggcacgc ggttgccgca gtatgctgac agtcatggct      300
tcatcctcat ttacccaagt actcctcaca tgagcaactg ctgggatgtg caaaaccccg      360
ctagcttgac tcatggtgcc ggtggtgatg ctcttggtat cgtcagcatg gtaaactacg      420
ccattaatcg gtacggagcc gaccgcgacc gcgtctacgc catgggcttc tcttccggtg      480
gcatgatgac caatgtgctg gcgggctcgt accccgatgt cttcgaggct ggggcggctt      540
actccggtgt tcctcatgct tgcttccttg gtatgtatcg ctctccttc catttctga      600
atactcatcg agggctcgga agcggtccgg tgttggcctg aatatcatga gcatttgctc      660
```

```
cttcaagcct ccagcgaact ctacgagcat ggggcctacc actctggaac cattgatcgt    720
gaattagcta atcatcctgc tcccttatag gtgctcccgc tgccactccg ttcagcccca    780
accaaacctg tgctcagggt ctgcagaaga cccccgagga atggggcaac cttgtgcgta    840
attcttaccc tggttacaat ggccgccggc cgcggatgca gatcacgcac ggcctgaacg    900
actggcttgt caggcctcag tgtgcctatg agactctcaa gcagtggtcc aacgttttgg    960
gtctggagct cactcggcaa gttacctctg gcaatggac gcagcatatt tatggtgatg    1020
ggacgaagtt agttggctat tttggccaag gagttggcca cgagccctca gtaaatgagg    1080
agcaactgtt gcggttcttt ggcattatca actaa                               1115
```

`<210>` SEQ ID NO 10
`<211>` LENGTH: 1080
`<212>` TYPE: DNA
`<213>` ORGANISM: Melanocarpus albomyces
`<220>` FEATURE:
`<221>` NAME/KEY: source
`<222>` LOCATION: 1..1080
`<223>` OTHER INFORMATION: /mol_type="DNA"
/organism="Melanocarpus albomyces"

`<400>` SEQUENCE: 10

```
atgctcgctc gaacgttcct cgggctcgcc gccacggcgg cgacgtgctt gggcgcctcg    60
ctgcagcagg tgaccaactt tggcaacaac ccgaccaaca tccagatgca catctatgtg    120
cctgacaggg tcgccagcaa cccagcaatc atcgtggcgg tgagtgctcg aagagcggcg    180
cttgctcacc ccctggaagt tctctgtgca tttggctcac ttgtgtcacc acgtaccagc    240
ttcatccctg cggcggcaat gcccagcagt ggttcggcgg caccggctg ccgtcgtacg    300 ccgaccagca cggcttcatc ctcatctacc ccagcactcc gcacatgagc aactgctggg    360
acgtgcacaa tccggccagc ttgacccatg gcagggcgg agatgcgctt ggcatcgtca    420
gcatggtgaa ctacgccctg aaccagtaca acggcgaccg caaccgcgtc tatgccatgg    480
gcttctcgtc gggcggcatg atgaccaacg tcctggcggg ctcgtacccc gacgtgttcg    540
aggctggcgc ggcctattct ggcgtgcccc atgcatgctt cttgggtacg tggtgattga    600
tgttgatgct gcggcctgtg ttggcggtgg tcgtggcgtt gtccctccgg cagcgagagt    660
ctcgacgacg gcgagatgac tgacgcatgt tcctcccgac dacaggtgca cctgccgcca    720
cgccgttcag ccccaaccag acctgcgccc agggcctcca aagacggag caggaatggg    780 gcgacctggt gcgcaactcg tatcccggct acacgggccg gcggccgcgc atgcagatca    840
cgcacggcct ggccgacttc ctggtgcggc cgcagtgcgc gtacgaggcg ctcaagcagt    900
ggtccaacgt gctgggagtc cagctcacgc gcgaagtgag gggcgtgccg tcgccgcagt    960
tcacgcagct catttacggc gacggcaccc agtctgcagg gattcctcgg ggacggcgtc    1020
ggtcacgagc cgtcggtcaa cgaggagcag atgctgaggt ttttcggcct gatcaactga    1080
```

`<210>` SEQ ID NO 11
`<211>` LENGTH: 289
`<212>` TYPE: PRT
`<213>` ORGANISM: Chaetomium thermophilum
`<220>` FEATURE:
`<221>` NAME/KEY: SOURCE
`<222>` LOCATION: 1..289
`<223>` OTHER INFORMATION: /mol_type="protein"
/organism="Chaetomium thermophilum"

`<400>` SEQUENCE: 11

```
Met His Leu Pro Ser Leu Leu Gly Leu Ala Ala Met Ala Ser Ser Cys
1               5                   10                  15

Leu Ala Ala Ser Leu Gln Gln Val Ser Asn Phe Gly Ser Asn Pro Thr
                20                  25                  30

Asn Ile Asn Met His Ile Tyr Val Pro Asp Arg Leu Ala Ser Lys Pro
            35                  40                  45

Pro Ile Ile Val Ala Leu His Pro Cys Gly Gly Asn Ala Gln Gln Trp
    50                  55                  60

Phe Ser Gly Thr Arg Leu Pro Gln Tyr Ala Asp Ser His Gly Phe Ile
65                  70                  75                  80

Leu Ile Tyr Pro Ser Thr Pro His Met Ser Asn Cys Trp Asp Val Gln
                85                  90                  95

Asn Pro Ala Ser Leu Thr His Gly Ala Gly Gly Asp Ala Leu Gly Ile
            100                 105                 110

Val Ser Met Val Asn Tyr Ala Ile Asn Arg Tyr Gly Ala Asp Arg Asp
        115                 120                 125

Arg Val Tyr Ala Met Gly Phe Ser Ser Gly Gly Met Met Thr Asn Val
    130                 135                 140

Leu Ala Gly Ser Tyr Pro Asp Val Phe Glu Ala Gly Ala Ala Tyr Ser
145                 150                 155                 160

Gly Val Pro His Ala Cys Phe Leu Gly Ala Pro Ala Ala Thr Pro Phe
                165                 170                 175

Ser Pro Asn Gln Thr Cys Ala Gln Gly Leu Gln Lys Thr Pro Glu Glu
            180                 185                 190

Trp Gly Asn Leu Val Arg Asn Ser Tyr Pro Gly Tyr Asn Gly Arg Arg
        195                 200                 205

Pro Arg Met Gln Ile Thr His Gly Leu Asn Asp Trp Leu Val Arg Pro
    210                 215                 220

Gln Cys Ala Tyr Glu Thr Leu Lys Gln Trp Ser Asn Val Leu Gly Leu
225                 230                 235                 240

Glu Leu Thr Arg Gln Val Thr Ser Gly Gln Trp Thr Gln His Ile Tyr
                245                 250                 255

Gly Asp Gly Thr Lys Leu Val Gly Tyr Phe Gly Gln Gly Val Gly His
            260                 265                 270

Glu Pro Ser Val Asn Glu Glu Gln Leu Leu Arg Phe Phe Gly Ile Ile
        275                 280                 285

Asn

<210> SEQ ID NO 12
<211> LENGTH: 271
<212> TYPE: PRT
<213> ORGANISM: Melanocarpus albomyces
<220> FEATURE:
<221> NAME/KEY: SOURCE
<222> LOCATION: 1..271
<223> OTHER INFORMATION: /mol_type="protein"
     /organism="Melanocarpus albomyces"

<400> SEQUENCE: 12

Met Leu Ala Arg Thr Phe Leu Gly Leu Ala Ala Thr Ala Ala Thr Cys
1               5                   10                  15

Leu Gly Ala Ser Leu Gln Gln Val Thr Asn Phe Gly Asn Asn Pro Thr
                20                  25                  30

Asn Ile Gln Met His Ile Tyr Val Pro Asp Arg Val Ala Ser Asn Pro
            35                  40                  45

Ala Ile Ile Val Ala Leu His Pro Cys Gly Gly Asn Ala Gln Gln Trp
```

```
                    50                    55                    60
Phe Gly Gly Thr Arg Leu Pro Ser Tyr Ala Asp Gln His Gly Phe Ile
 65                  70                  75                  80

Leu Ile Tyr Pro Ser Thr Pro His Met Ser Asn Cys Trp Asp Val His
                 85                  90                  95

Asn Pro Ala Ser Leu Thr His Gly Gln Gly Gly Asp Ala Leu Gly Ile
                100                 105                 110

Val Ser Met Val Asn Tyr Ala Leu Asn Gln Tyr Asn Gly Asp Arg Asn
            115                 120                 125

Arg Val Tyr Ala Met Gly Phe Ser Ser Gly Gly Met Met Thr Asn Val
        130                 135                 140

Leu Ala Gly Ser Tyr Pro Asp Val Phe Glu Ala Gly Ala Ala Tyr Ser
145                 150                 155                 160

Gly Val Pro His Ala Cys Phe Leu Gly Ala Pro Ala Ala Thr Pro Phe
                165                 170                 175

Ser Pro Asn Gln Thr Cys Ala Gln Gly Leu Gln Lys Thr Glu Gln Glu
                180                 185                 190

Trp Gly Asp Leu Val Arg Asn Ser Tyr Pro Gly Tyr Thr Gly Arg Arg
            195                 200                 205

Pro Arg Met Gln Ile Thr His Gly Leu Ala Asp Phe Leu Val Arg Pro
        210                 215                 220

Gln Cys Ala Tyr Glu Ala Leu Lys Gln Trp Ser Asn Val Leu Gly Val
225                 230                 235                 240

Gln Leu Thr Arg Glu Gly Phe Leu Gly Asp Gly Val Gly His Glu Pro
                245                 250                 255

Ser Val Asn Glu Glu Gln Met Leu Arg Phe Phe Gly Leu Ile Asn
                260                 265                 270
```